US008932296B2

(12) United States Patent
Neary et al.

(10) Patent No.: US 8,932,296 B2
(45) Date of Patent: Jan. 13, 2015

(54) SPINAL ROD PERSUADER

(75) Inventors: Douglas Wayne Neary, Santa Ana, CA (US); James Monroe Davenport, Kingman, AZ (US)

(73) Assignee: Oak Tree Engineering LLC, Huntington Beach, CA (US)

( * ) Notice: Subject to any disclaimer, the term of this patent is extended or adjusted under 35 U.S.C. 154(b) by 169 days.

(21) Appl. No.: 13/246,631

(22) Filed: Sep. 27, 2011

(65) Prior Publication Data

US 2013/0079827 A1 Mar. 28, 2013

(51) Int. Cl.
*A61B 17/70* (2006.01)
*A61B 17/88* (2006.01)

(52) U.S. Cl.
CPC ......... *A61B 17/7086* (2013.01); *A61B 17/7077* (2013.01); *A61B 17/8869* (2013.01)
USPC ...................................... 606/86 A

(58) Field of Classification Search
USPC ............................. 606/86 R, 86 A
See application file for complete search history.

(56) References Cited

U.S. PATENT DOCUMENTS

| | | | |
|---|---|---|---|
| 5,449,361 A | 9/1995 | Preissman | |
| 5,536,270 A | 7/1996 | Songer et al. | |
| 5,782,831 A * | 7/1998 | Sherman et al. | 606/86 A |
| 6,123,707 A | 9/2000 | Wagner | |
| 6,146,386 A * | 11/2000 | Blackman et al. | 606/103 |
| 6,648,888 B1 | 11/2003 | Shluzas | |
| 6,660,006 B2 | 12/2003 | Markworth et al. | |
| 6,689,140 B2 * | 2/2004 | Cohen | 606/103 |
| 7,491,207 B2 | 2/2009 | Keyer et al. | |
| 7,572,281 B2 | 8/2009 | Runco et al. | |
| 7,618,444 B2 | 11/2009 | Shluzas | |
| 7,776,040 B2 | 8/2010 | Markworth et al. | |
| 7,887,541 B2 | 2/2011 | Runco et al. | |
| 8,162,946 B2 * | 4/2012 | Baccelli et al. | 606/86 A |
| 2003/0199872 A1 | 10/2003 | Markworth et al. | |
| 2003/0225408 A1 | 12/2003 | Nichols et al. | |
| 2004/0049191 A1 | 3/2004 | Markworth et al. | |
| 2004/0147636 A1 | 7/2004 | Rosenberg et al. | |
| 2004/0237275 A1 | 12/2004 | Cournoyer et al. | |
| 2005/0033299 A1 | 2/2005 | Shluzas | |
| 2005/0228392 A1 | 10/2005 | Keyer et al. | |
| 2006/0089651 A1 | 4/2006 | Trudeau et al. | |
| 2006/0293690 A1 | 12/2006 | Abdelgany | |
| 2007/0278339 A1 * | 12/2007 | McMahan | 242/439 |
| 2008/0004629 A1 | 1/2008 | Nichols et al. | |
| 2008/0015601 A1 | 1/2008 | Castro et al. | |
| 2008/0154277 A1 | 6/2008 | Machalk et al. | |

(Continued)

OTHER PUBLICATIONS

Zimmer Spine, Universal Clamp® Spinal Fixation System: Surgical Technique, Aug. 2009, 24 pages.

(Continued)

*Primary Examiner* — Ellen C Hammond
(74) *Attorney, Agent, or Firm* — Knobbe Martens Olson & Bear LLP

(57) ABSTRACT

Methods, systems, and devices for pulling a spinal vertebra toward a spinal rod are provided. One spinal rod persuasion system includes a cord configured to engage a pedicle screw installed in a spinal vertebra. The system also includes a tensioner configured to engage the cord and a spinal rod, and to apply tension to the cord to pull the pedicle screw toward the spinal rod. One method includes installing a pedicle screw in a spinal vertebra, affixing a cord to the pedicle screw, coupling the cord to a tensioner, coupling a spinal rod to the tensioner, and pulling the pedicle screw toward the spinal rod.

18 Claims, 10 Drawing Sheets

(56) References Cited

U.S. PATENT DOCUMENTS

| | | |
|---|---|---|
| 2008/0228233 A1 | 9/2008 | Hoffman et al. |
| 2008/0234765 A1 | 9/2008 | Frasier et al. |
| 2009/0018593 A1 | 1/2009 | Barrus et al. |
| 2009/0228055 A1 | 9/2009 | Jackson |
| 2010/0228302 A1 | 9/2010 | Dauster et al. |
| 2011/0034961 A1 | 2/2011 | Runco et al. |
| 2011/0087298 A1 | 4/2011 | Jones |
| 2011/0118791 A1 | 5/2011 | Nunley et al. |
| 2011/0144695 A1 | 6/2011 | Rosenberg et al. |

OTHER PUBLICATIONS

International Search Report and Written Opinion in Int'l App. No. PCT/US2012/057128 dated Feb. 26, 2013.

\* cited by examiner

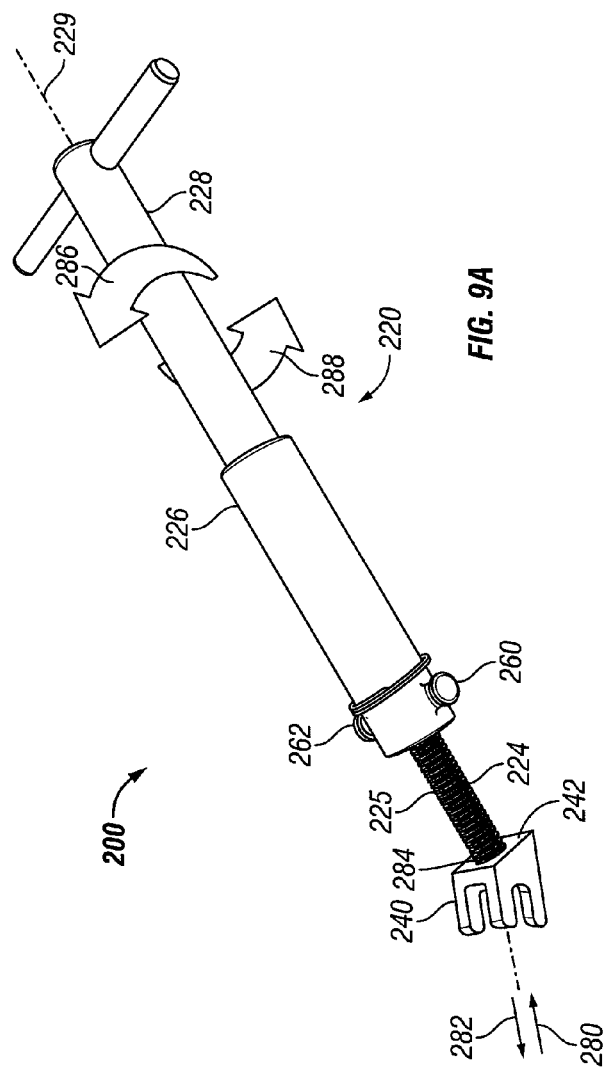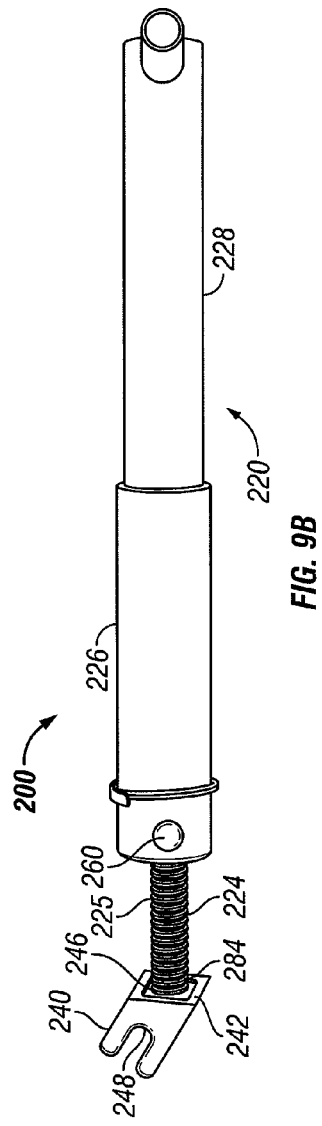

SPINAL ROD PERSUADER

BACKGROUND

1. Field of the Invention

The field of the invention relates to spinal surgery, and more particularly to methods, systems, and devices for persuading a spinal rod to a pedicle screw.

2. Description of the Related Art

Spinal surgery may be used to alleviate back pain and correct spinal disorders due to various causes including spinal disease, abnormalities, or trauma. Surgeons install screws and spinal rods during some forms of spinal surgery to achieve the desired anatomical configuration of a patient's spine. The procedure may include installing pedicle screws, or other forms of vertebral anchoring devices, including hooks for example, into the pedicle of the patient's spinal vertebra. These anchoring devices act as firm anchor points to manipulate and stabilize the spine. The surgeon may also install spinal rods and couple them to the anchoring devices, providing a construct to hold the spine in the desired position. The spinal rods are generally positioned parallel to the spine and coupled to anchoring devices installed on adjacent vertebrae. After coupling the spinal rod to an anchoring device, surgeons generally hold the construct in place with a set screw or fastener. The construct may restrict movement to allow vertebral fusion. The construct may also be used to change the alignment of the spine. By fusing and/or aligning the spinal vertebrae, surgeons can reduce back pain and promote healing in the patient.

Surgeons often encounter difficulty in persuading a spinal rod toward an installed anchoring device in order to couple the spinal rod to the anchoring device. Disadvantages associated with prior art reduction methods and devices include pulling on the anchoring device along its longitudinal axis and risking destabilization of the construct; the inability to manipulate the spinal vertebrae in more than one direction; and incompatibility with multiple types of anchoring devices. Thus, methods, systems, and devices to efficiently and reliably reduce a spinal rod to an anchoring device are desired and remain a significant challenge in some forms of spinal surgery.

SUMMARY OF CERTAIN EMBODIMENTS

The systems, methods, and devices of the invention each have several aspects, no single one of which is solely responsible for its desirable attributes. Without limiting the scope of this invention, its more prominent features will now be discussed briefly. After considering this discussion, and particularly after reading the section entitled "Detailed Description" one will understand how the features of this invention provide advantages over other methods, systems, and devices for spinal surgery.

According to one embodiment of the invention, a method of persuading a spinal vertebra toward a spinal rod is provided. The method includes affixing a cord to a pedicle screw installed in the spinal vertebra; coupling the cord to a tensioner; coupling the spinal rod to the tensioner; and pulling the pedicle screw toward the spinal rod.

According to another embodiment of the invention, a system for moving a pedicle screw installed in a spinal vertebra toward a spinal rod is provided. The system includes a cord including a first portion configured to wrap around a base of the pedicle screw. The system also includes a tensioner configured to engage the spinal rod. The cord also includes a second portion configured to couple to the tensioner, the tensioner configured to pull the second portion of the cord, thereby moving the pedicle screw toward the spinal rod.

BRIEF DESCRIPTION OF THE DRAWINGS

FIG. 9A is a perspective view of a spinal rod persuader system according to another embodiment.

FIG. 9B is a perspective side view of the spinal rod persuader system of FIG. 9A.

DETAILED DESCRIPTION

Any feature or combination of features described herein are included within the scope of the present invention provided that the features included in any such combination are not mutually inconsistent as will be apparent from the context, this description, and the knowledge of one skilled in the art. In addition, any feature or combination of features may be specifically excluded from any embodiment of the present invention. For purposes of summarizing the present invention, certain aspects, advantages, and novel features of the present invention are described herein. Of course, it is to be understood that not necessarily all such aspects, advantages, or features will be present in any particular embodiment of the present invention.

In reference to the disclosure herein, for purposes of convenience and clarity only, directional terms, such as top, bottom, left, right, up, down, upper, lower, over, above, below, beneath, rear, and front may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

Various spinal vertebral anchoring devices are described herein. Anchoring devices described herein may include any suitable spinal vertebral anchoring device, including, but not limited to, pedicle screws, pedicle hooks, transverse process hooks, and sublaminar hooks. Thus, the systems described herein are not limited to use with pedicle screws, and can be used with any suitable spinal vertebral anchoring device. Various spinal rod persuader systems are also described in relation to spinal surgery. The systems, devices, and methods described herein may be adapted for use in other parts of the body, including for example, reducing fractures in a patient's extremities.

Spinal Rod Persuader System

Figure 1:
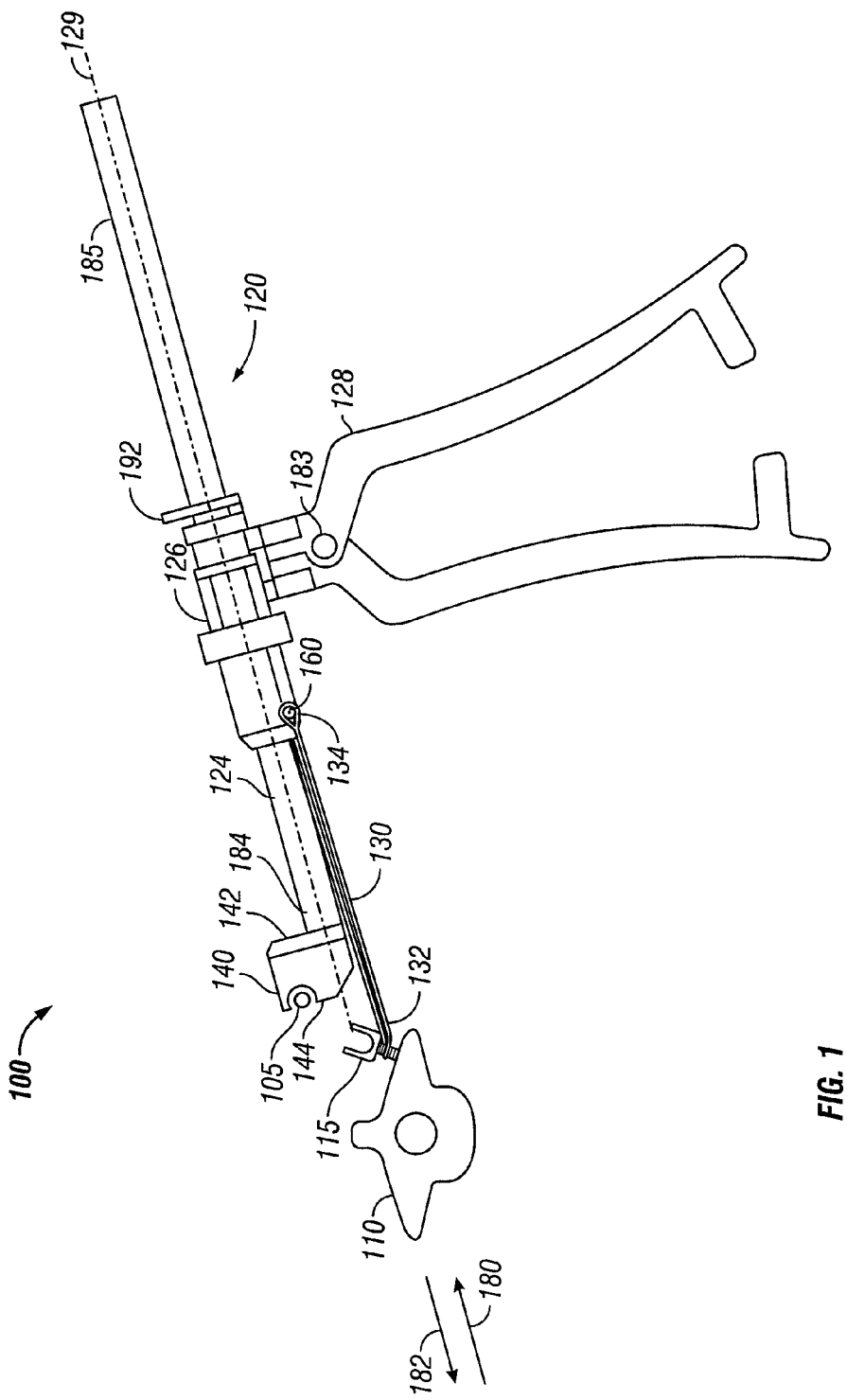
FIG. 1 is an elevational view of an embodiment of a spinal rod persuader system.

FIG. 1 is an elevational view of a spinal rod persuader system 100 for persuading a spinal rod 105 toward a spinal vertebra 110, allowing a surgeon to couple the spinal rod 105 to a pedicle screw system installed in the spinal vertebra 110. In some aspects, the rod 105 is a rigid cylindrical structure configured to seat in channeled cups 115 provided as part of a pedicle screw system installed in adjacent vertebrae to stabilize the spine. The persuader system 100 engages both the pedicle screw system and the spinal rod 105, and pulls the spinal vertebra 110 towards the spinal rod 105.

The persuader system 100 includes a tensioner 120, a cord 130, and an anvil 140. The cord 130 is configured to engage the pedicle screw and the tensioner 120. For example, a first portion 132 of the cord 130 can be coupled to the pedicle screw. In some aspects, the first portion 132 of the cord 130 is configured to wrap around a portion of the pedicle screw beneath the cup 115, but above the surface of the vertebral body. This will be referred to as the "base" of the pedicle screw system. A second portion 134 of the cord 130 can be coupled to the tensioner 120. The anvil 140 is configured to engage the spinal rod 105 and the tensioner 120. In some aspects, the anvil 140 includes a first side 142 coupled to the tensioner 120 and a second side 144 coupled to the spinal rod 105. The first side 142 of the anvil 140 can be coupled to the axial member 124 of the tensioner 120. The second side 144 of the anvil 140 can be configured to accept spinal rods 105 of different sizes and shapes.

The tensioner 120 includes an axial member 124, a slider 126, and a handle 128. The tensioner 120 can tension the cord 130 coupled to the pedicle screw to move the pedicle screw toward the spinal rod 105 engaged in the anvil 140. In some aspects, the tensioner 120 can be configured to pull the second portion 134 of the cord 130, thereby moving the pedicle screw toward the spinal rod 105. For example, in one aspect, the second portion 134 of the cord 130 is coupled to the slider 126 of the tensioner 120. The tensioner 120 can tension the cord 130 by moving the slider 126 along a longitudinal axis 129 of the tensioner 120, thereby pulling the second portion 134 of the cord 130.

The axial member 124 is substantially cylindrical and can be hollow or solid in construction. A first end 184 of the axial member 124 can be coupled to an anvil 140, which is configured to engage the spinal rod 105. The system 100 can include a plurality of anvils 140 of varying sizes and shapes. The anvil 140 can be removable and replaceable from the end of the axial member 124, such that different sizes and or shapes of anvil 140 can be attached and used depending on the rod 105 configuration, relative position of the spine, etc.

The slider 126 includes a substantially cylindrical hollow portion to slidably engage and accept the axial member 124. The slider 126 is configured to slide on the axial member 124 along the longitudinal axis 129. A ratchet mechanism (not shown) connects the handle 128 and the slider 126 such that activation of the handle 128 about a hinge 183 advances the axial member 124 relative to the slider 126 along the longitudinal axis 129. The ratchet mechanism may resemble that of a caulking gun, in which squeezing a handle advances a central plunger seated against a tube of caulking relative to a housing in order to push sealant through the tube. In one aspect, squeezing the handle 128 advances the axial member 124 within the slider 126 along the axial member 124 using a mechanism similar to that of a caulking gun. When the anvil 140 is engaged to the rod 105, repeated operation of the handle 128 will incrementally force the slider 126 back in the direction 180, thereby applying tension to the cord 130 coupled to the slider 126 and pulling the spinal vertebra 110 towards the spinal rod 105 engaged in the anvil 140. Between compressions of the handle, motion of the slider 126 in the opposite direction can be stopped with a spring loaded stop plate 192, also a common feature on caulking guns.

The tensioner 120 can be operated with a portion of the tensioner 120 disposed inside the spinal area of the patient, and a portion disposed outside the spinal area for ease of manipulation by the surgeon. For example, the cord 130, the anvil 140, and the first end 184 of the axial member 124 can be inserted into an incision in the spinal area, while the slider 126, the handle 128, and a second end 185 of the axial member 124 can remain external to the patient.

Embodiments of the tensioner 120 may be made of any suitable material, including but not limited to stainless steel. In some aspects, the handle 128 is detachable from the slider 126 and may be affixed to the slider 126 in more than one angular orientation. The tensioner 120 can also include a force limiting device to ensure the surgeon does not apply excessive force to either the spinal rod 105 or to the pedicle screw system. In one embodiment, the tensioner 120 includes a mechanism preventing further movement of the slider 126 along the axial member 124 after a certain degree of tension in the cord 130 is achieved. In some embodiments, the tension level may be adjusted by the surgeon based on the conditions present during the procedure.

The tensioner 120 allows the surgeon to squeeze the handle 128 and advance the slider 126 using only one hand, keeping the surgeon's other hand free during a reduction procedure. The ability to adjust the angle at which the handle 128 is attached to the tensioner 120 also advantageously allows for ease of manipulation by the surgeon and adjustment of the tensioner 120 based on a particular patient's needs.

Accordingly, embodiments of the system 100 can be used persuade a spinal vertebra toward a spinal rod. One spinal rod persuasion method includes installing a pedicle screw in the spinal vertebra 110, affixing the cord 130 to the pedicle screw, coupling the cord 130 to the tensioner 120, coupling a spinal rod 105 to the tensioner 120, and pulling the pedicle screw toward the spinal rod 105.

Cord

Figure 2A:
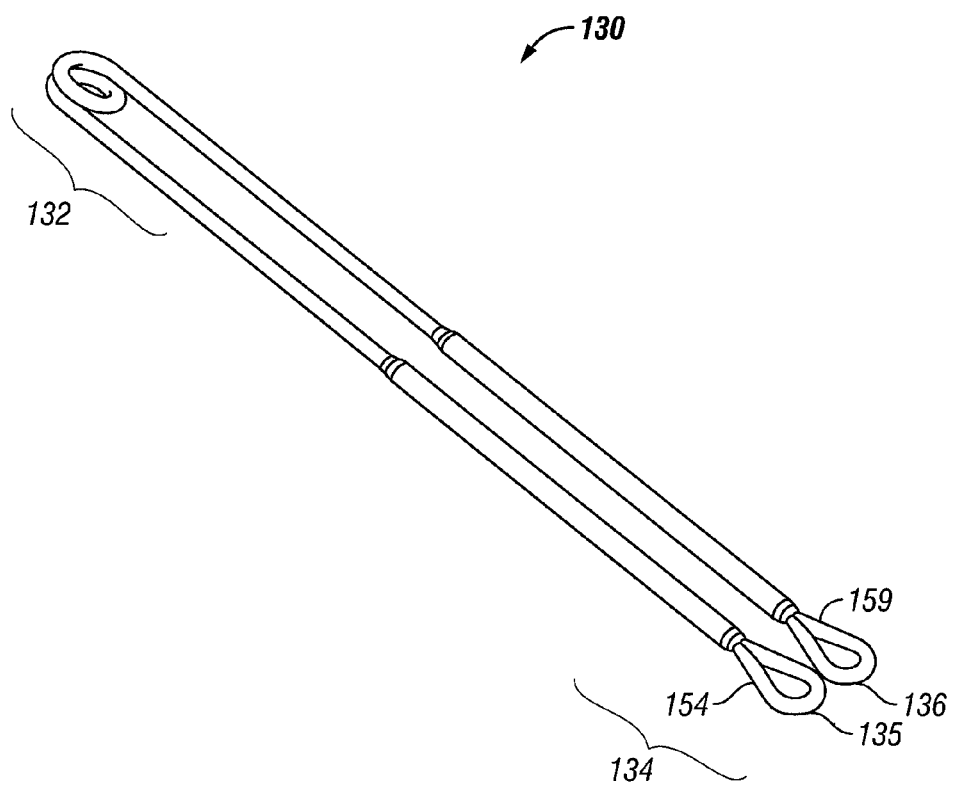
FIG. 2A is a perspective view of an embodiment of a cord usable in the spinal rod persuader system of FIG. 1.

FIG. 2A is a perspective view of an embodiment of a cord 130 usable in the spinal rod persuader system 100 of FIG. 1. A first portion 132 of the cord 130 can be affixed to the pedicle screw beneath cup 115 and a second portion 134 of the cord 130 can be coupled to the tensioner 120. In some aspects, the first portion 132 includes a middle section of the cord 130. The second portion 134 includes a first end 135 of the cord 130 and a second end 136 of the cord 130. The first end 135 and the second end 136 are configured to couple to the tensioner 120 of FIG. 1.

Figure 2B:
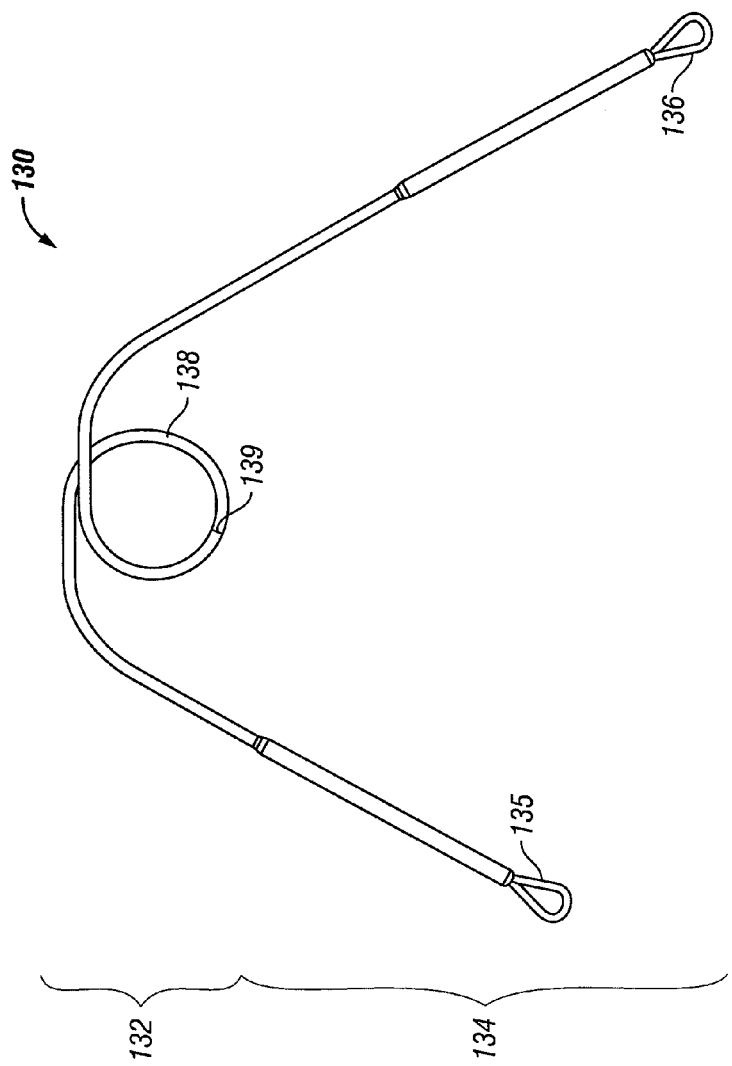
FIG. 2B is an elevational view of the cord of FIG. 2A.

Embodiments of the cord 130 can be affixed to the pedicle screw in various ways. FIG. 2B is an elevational view of the cord of FIG. 2A illustrating a loop or lasso 138 in the first portion 132 of the cord 130. The first portion 132 can include a middle section of the cord 130, and the loop 138 can be formed in the middle section of the cord 130. In some embodiments, the loop 138 can be formed by the surgeon. In other embodiments, the loop 138 can be preformed in the cord 130 to facilitate installation onto the pedicle screw.

In one embodiment illustrated in FIGS. 2A and 2B, the surgeon forms the loop 138 in the cord 130. The cord 130 is affixed to the pedicle screw by looping the first end 135 or the second end 136 of the cord 130 around the pedicle screw, thereby forming the loop 138 in the cord 130 with the pedicle screw centered in the middle of the loop 138. The cord 130 can be cinched by pulling the first end 135 and/or the second end 136 to pull the loop 138 tight around the pedicle screw, affixing the cord 130 to the pedicle screw. The loop 138 includes one loop in the embodiment illustrated in FIGS. 2A and 2B, but the cord 130 can be wrapped around the pedicle screw more than once such that the loop 138 includes two or more loops around the pedicle screw.

The cord 130 can include a mark 139 generally located at a midpoint of the cord 130. The mark 139 can be used to ensure the loop 138 is generally centered around a midpoint of the cord 130. For example, the surgeon can loop the first end 135 around the pedicle screw while holding the second end 136 secure, then adjust or re-position the loop 138 so that the mark 139 is centered on the pedicle screw, ensuring the loop 138 is generally located at the midpoint of the cord 130. The surgeon can then cinch the loop 138 tight around the pedicle screw. The mark 139 can also ensure approximately equal lengths of the cord 130 extend from the pedicle screw on either side.

In some aspects, the pedicle screw includes a head and a base. The head can have a larger diameter than the base. The head can be configured to accept the rod 105 and the base can be installed in the spinal vertebra 110. The loop 138 can wrap around the base, or a smaller diameter portion, of the pedicle screw. The head, or larger diameter portion, of the pedicle screw can prevent the cord 130 from being pulled up and off of the pedicle screw after installation around the base of the pedicle screw. Additionally, the cord 130 can have a diameter that enables the cord 130 to wrap around the base of the pedicle screw, while also handling tensioning loads involved in the persuasion procedure. The cord 130 may be ⅛" or less in diameter and may be approximately 12 inches in length. Other diameters and lengths are possible. Cord of sufficient strength is commercially available in a variety of diameters and dimensions.

Figure 3:
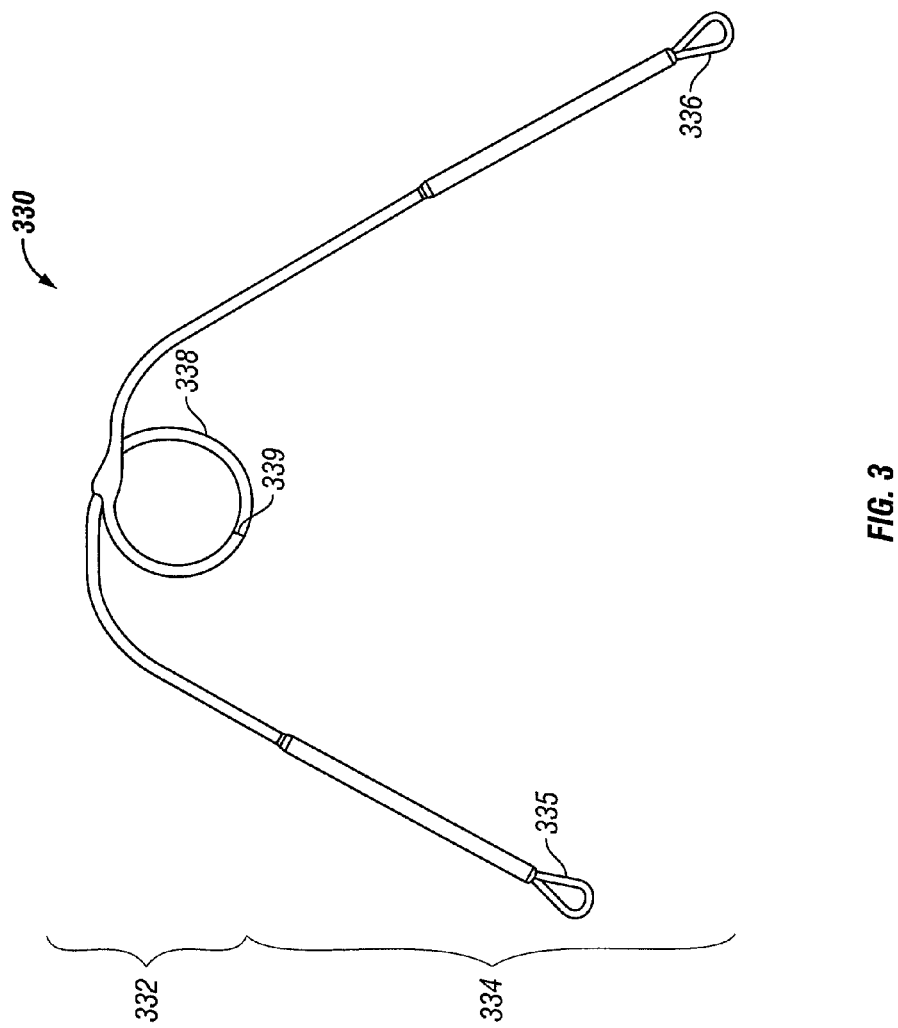
FIG. 3 is an elevational view of another embodiment of a cord usable in the spinal rod persuader system of FIG. 1.

FIG. 3 is an elevational view of another cord 330 usable in the system 100 of FIG. 1, in a loop 338 is preformed in a first portion 332 of the cord 330. The loop 338 can include a lasso 338. In some aspects, the lasso 338 is generally located at a midpoint of the cord 330. The cord 330 may or may not include a mark 339 generally located at a midpoint of the cord 330. The lasso 338 can be formed in the cord 330 in a variety of ways. For example, the lasso 338 can be formed by splicing a first end 335 of the cord 330 into a portion of the fiber weave of the cord 330.

To affix the cord 330 to the pedicle screw, the surgeon can place the lasso 338 over the head of the pedicle screw, position the lasso 338 loosely around the base of the pedicle screw, and apply tension to the first end 335 and the second end 336 to cinch the lasso 338 around the base of the pedicle screw. In one aspect, the surgeon applies tension to the first end 335 and the second end 336 by hand. In another aspect, the tensioner 120 of FIG. 1 applies tension to the first end 335 and the second end 336. The portion of the cord 330 through which the first end 335 is spliced to form the lasso 338 can be offset from the midpoint of the cord 330 to ensure both ends of the cord 330 are approximately equidistant from the pedicle screw when the ends 335, 336 are tensioned.

Figure 4:
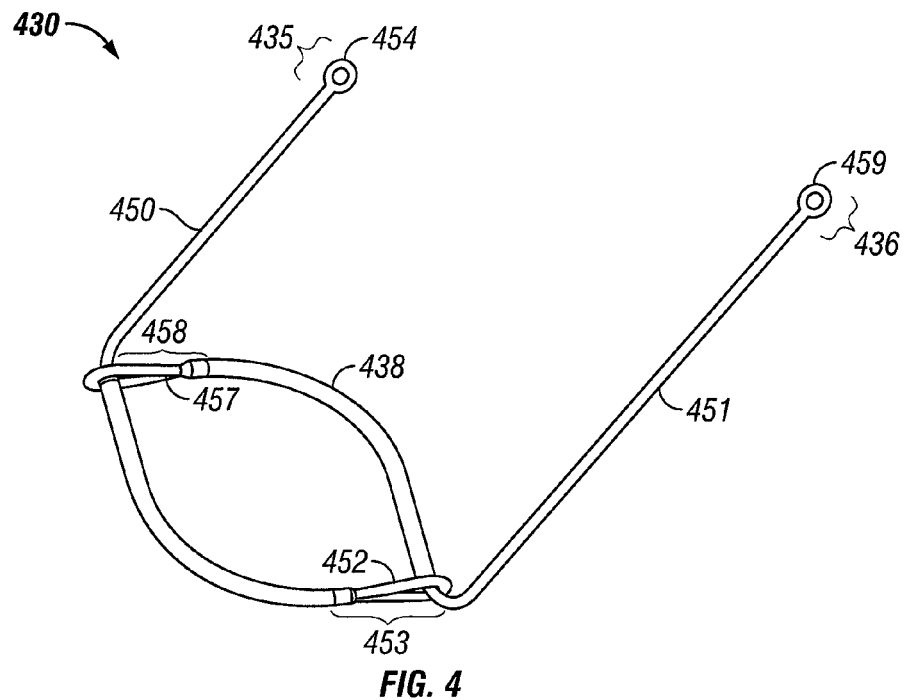
FIG. 4 is a perspective view of yet another embodiment of a cord usable in the spinal rod persuader system of FIG. 1.

FIG. 4 is a perspective view of yet another cord 430 usable in the system 100 of FIG. 1, in which a first line 450 and a second line 451 are coupled to form the cord 430. The lines 450, 451 can form a loop 438 that can be placed around the base of a pedicle screw. The loop 438 can include a double-strand lasso 438. The first line 450 can include a first connector 452 at a first end 453 and second connector 454 at a second end 435. The second line 451 can include a first connector 457 at a first end 458 and a second connector 459 at a second end 436. The first line 450 passes through the first connector 457 of the second line 451, and the second line 451 passes through the first connector 452 of the first line 450, forming the lasso 438.

The connectors 452, 454, 457, 459 can include but are not limited to eye splices formed in the ends of the lines 450, 451. Alternatively, the connectors 452, 454, 457, 459 can include loops that are affixed to the ends of the lines 450, 451. The loops can be affixed to the lines in a number of ways, including but not limited to stitching, gluing, or melting the loops onto the ends of the lines 450, 451.

The lasso 438 can be placed over the head of the pedicle screw, and the cord 430 can be cinched around the pedicle screw by applying tension simultaneously to the second end 435 and the second end 436. Applying tension can include pulling the ends 435, 436 in a direction away from the pedicle screw. Alternatively, the second end 435 can be held secure while the second end 436 is tensioned to close the double-strand lasso 438 around the base of the pedicle screw. The tensioner 120 of FIG. 1 can be used to apply tension to the second ends 435, 436.

Figure 5:
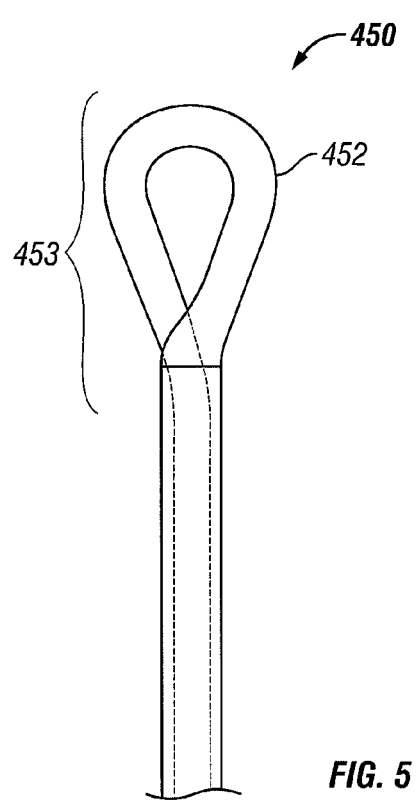
FIG. 5 is an elevational view of an embodiment of a connector of a cord usable in the spinal rod persuader system of FIG. 1.

FIG. 5 is an elevational view of an embodiment of a connector 452 of the line 450 of FIG. 4. The line 450 can comprise multi-stranded rope or line, and the connector 452 can include an eye splice 452. Embodiments of the cords 130 and 330 can also include eye splice connectors at their respective ends 135, 136, 335, 336. The eye splice 452 can create a permanent loop in the first end 453 of the line 450 by splicing strands in a working end of the line 450 into a working part of the line 450, forming a loop. In the embodiment illustrated in FIG. 5, the entire working end of the line 450 is spliced into a working part of the line 450, but other configurations are possible. The eye splice 452 can form a strong connection point at the first end 453 of the line 450, while minimally reducing the ultimate strength of the line 450. In some embodiments, the presence of the eye splice 452 reduces the ultimate strength of the line 450 by approximately 10%.

Embodiments of the cords 130, 330, and 430 can be made of any suitable material, including but not limited to polyether ether ketone (PEEK), polyethylene, polypropylene, nylon. The cords 130, 330, and 430 can be made of ultra-high-molecular-weight polyethylene materials, including but not limited to Dyneema® and Spectra®. In one embodiment, the cord 130 includes a suture material. The cord 130 may consist of a monofilament or a weave material. The weave may be composed of a circular weave or a linear fiber pattern.

In some embodiments the cord is disposable, allowing for one use with the tensioner 120 and then being replaced for subsequent procedures using the same tensioner 120. Disposable cords 130 can advantageously reduce opportunities for contamination and infection. It is one advantageous aspect of the systems and methods described herein that the cord is removable from the pedicle screw at the conclusion of the procedure, and therefore the reducing system need not introduce an additional component which is implanted into the body and remains after the surgery. The cord can have a lubricious quality. For example, embodiments of the cord 130 can be formed of a lubricious material or include a lubricious coating. Additionally, the cord 130 can be compatible for use with multiple pedicle screw and anchoring devices available from different manufacturers.

The cord 130 can advantageously be oriented in multiple configurations relative to the spinal rod 105. Referring again to FIG. 1, for example, both the first end 135 and the second end 136 (not shown) of the cord 130 pass under the rod 105. In another embodiment, the first end 135 and the second end 136 of the cord 130 pass over a top side of the rod 105.

Coupling the Cord to the Tensioner

Eye Splice Connector

Embodiments of the cord 130 can be coupled to the tensioner 120 in a number of ways, including but not limited to coupling an eye splice connector of the cord 130 to a peg on the slider 126, coupling a toothed strip of the cord 130 to a ratchet system of the slider 126, and coupling an end of the cord 130 to a clamping structure of the slider 126.

Referring again to FIGS. 1 and 2A, embodiments of the cord 130 can include connectors configured to couple to the tensioner 120. The cord 130 can include a connector 154 at the first end 135 and a second connector 159 at the second end 136. The connectors 154, 159 can include eye splices 154, 159 configured to couple to the slider 126 of the tensioner 120. In one embodiment, the slider 126 includes a first peg 160 and a second peg 162 on the other side (not shown in FIG. 1). The eye splices 154, 159 can be placed over the pegs 160, 162 to couple the cord 130 to the tensioner 120. In some aspects, the pegs 160, 162 are substantially cylindrical and extend outward from the slider 126 in a direction generally perpendicular to the longitudinal axis 129 of the tensioner 120. The pegs 160, 162 can include beveled surfaces and/or locking mechanisms to hold the ends 134, 135 of the cord 130 affixed to the pegs 160, 162 during a reduction procedure. The slider 126 can move along the longitudinal axis 129 of the tensioner 120, moving the pegs 160, 162 in a general direction 180 away from the rod 105, and apply tension to the ends 134, 135 of the cord 130.

In some embodiments, the location of the pegs 160, 162 relative to the ends 135, 136 can be adjusted by rotating the slider 126 about the longitudinal axis 129. Changing the location of the pegs 160, 162 can alter the position of cord 130 relative to the tensioner 120.

Ratchet System

Figures 6A, 6B:
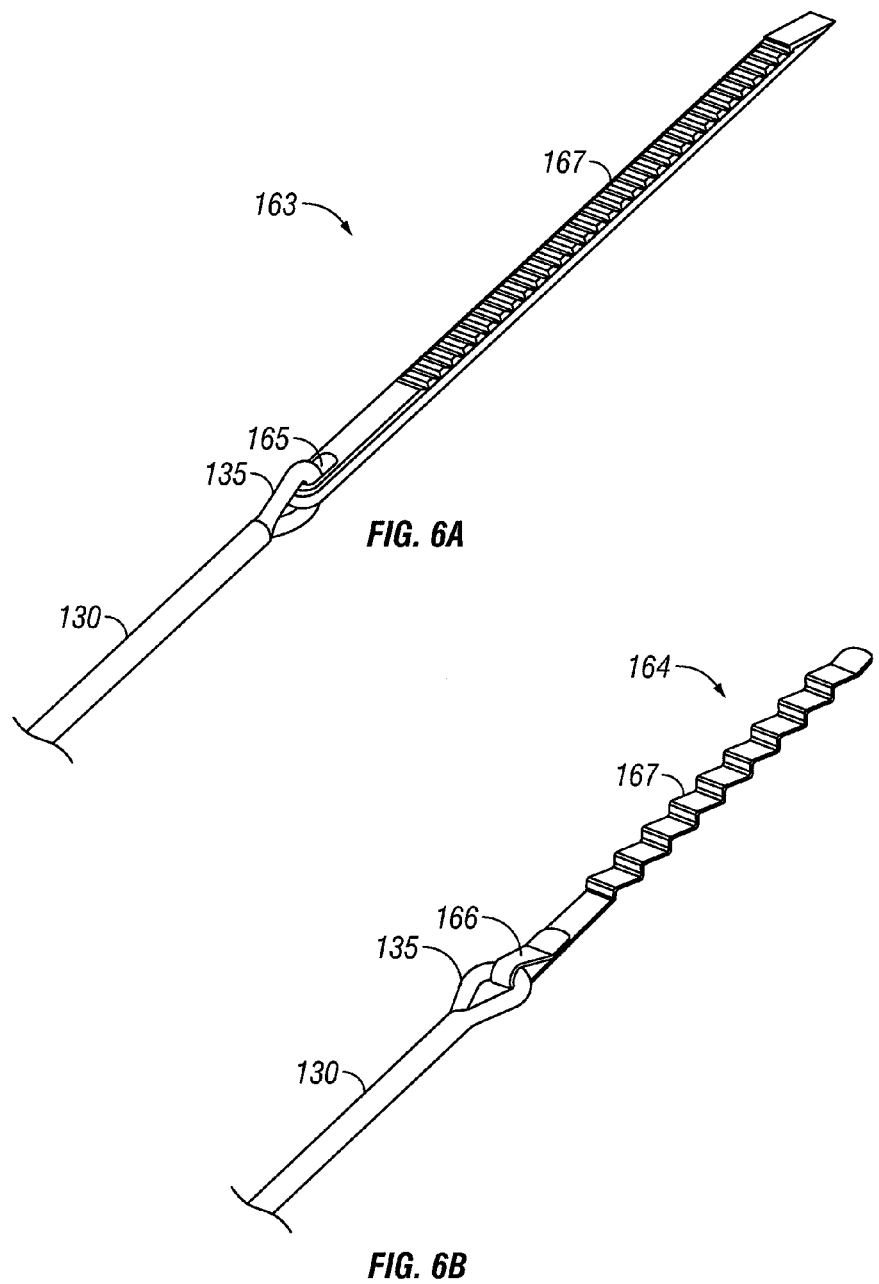
FIG. 6A is a perspective view of an embodiment of a toothed strip of the cord of FIG. 2A.
FIG. 6B is a perspective view of another embodiment of a toothed strip of the cord of FIG. 2A.
Figure 7:
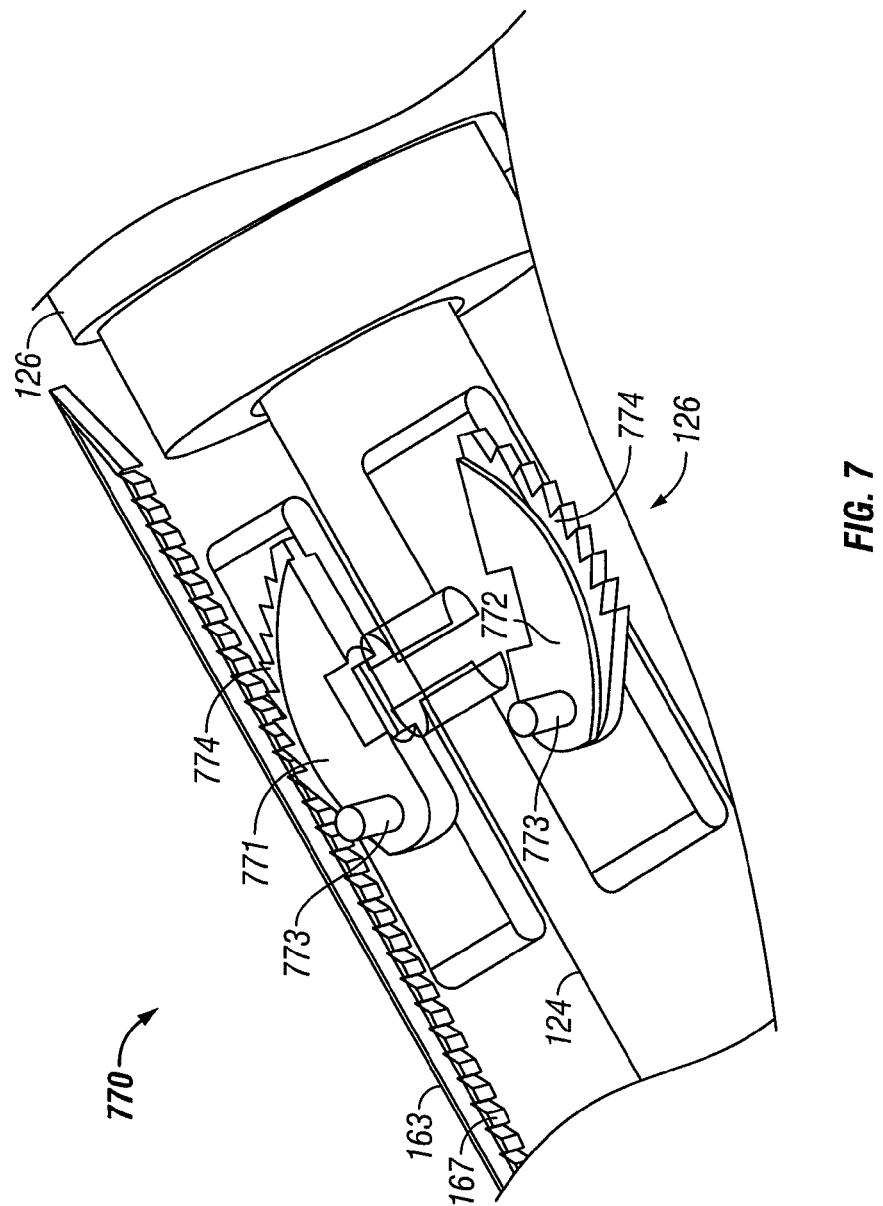
FIG. 7 is a partial perspective view of an embodiment of a ratchet system of the spinal rod persuader system of FIG. 1.

FIG. 6A is a perspective view of an embodiment of a toothed strip 163 of the cord of FIG. 2A. FIG. 6B is a perspective view of another embodiment of a toothed strip 164 of the cord of FIG. 2A. FIG. 7 is a partial perspective view of an embodiment of a ratchet system 770 of the spinal rod persuader system 100 of FIG. 1, with an outer casing of the system 770 removed to show internal features. Referring now to FIG. 6A, the first end 135 of the cord 130 can be coupled to a first toothed strip 163. The second end 136 of the cord 130 (not shown in FIG. 6A) can also be coupled to a second toothed strip 163. According to an alternative embodiment illustrated in FIG. 6B, the first end 135 of the cord 130 can be coupled to a first toothed strip 164. The second end 136 of the cord 130 (not shown in FIG. 6B) can be coupled to a second toothed strip 164. The toothed strips 163, 164 include teeth 167 along one or more surfaces. The toothed strips 163, 164 can be coupled to the slider 126 of the tensioner 120 using a ratchet system described below with reference to FIG. 7. The toothed strips 163, 164 can transfer tension forces applied by the tensioner 120 to the cord 130.

Referring again to FIG. 6A, the toothed strip 163 includes a connector 165 that couples the toothed strip 163 to the first end 135 of the cord 130. The connector 165 includes an opening formed in the toothed strip 163. Referring to FIG. 6B, the toothed strip 164 includes a different connector 166. The connector 166 can be formed by inserting an end of the toothed connectors 164 through an eye splice 154 of the cord 130 and affixing the end to the toothed connector 164. Other connector arrangements are possible.

Embodiments of the toothed strips 163, 164 may be made of any suitable material, including but not limited to metal and/or plastic. For example, embodiments of the toothed strip 163 may be molded from one piece of injection-molded plastic. Embodiments of the toothed strip 164 can be manufactured through a stamping process.

FIG. 7 illustrates a ratchet system 770 that can be used to couple the cord 130 to the tensioner 120. The slider 126 of the tensioner 120 can include the ratchet system 770 to engage toothed strips coupled to the ends 135, 136 of the cord 130. The first toothed strip 163 is coupled to the first end 135 of the cord 130 (not shown in FIG. 7). The ratchet system 770 is shown engaging the first toothed strip 163, but the system 770 can be configured to engage second toothed strip 163 coupled to the second end 136 of the cord 130, toothed strips 164, and other configurations of toothed strips.

The ratchet system 770 includes pivoting, spring-loaded pawls 771, 772 coupled to the slider 126. In one aspect, the pawls 771, 772 are connected to the slider 126 at posts 773. The pawls 771, 772 include teeth 774 that engage the teeth 167 of the toothed strip 163 when the toothed strip 163 is inserted in a direction 180 into the ratchet system 770. For example, toothed strips 163 connected to the first end 135 and the second end 136 of the cord 130 can be inserted into the ratchet system 770 so that both ends 135, 136 extend evenly from the pedicle screw and there is little to no slack in the cord 130. In some aspects, the ratchet system 770 allows the surgeon to compensate for one side of the cord 130 being longer than the other side due to an off-center installation of the cord 130 around the pedicle screw, as each toothed strip 163 is independently installed and can be pulled through the ratchet system 770 a different distance than the other toothed strip 163. The teeth 774 of the pawls 771, 772 can engage the teeth 167 of the toothed strips 163 to prevent movement of the toothed strips 163 back out of the ratchet system 770 in a direction 182. As a result, the ends 135, 136 of the cord 130 cannot be removed from the system 770 by pulling on the ends 135, 136 in the direction 182.

In some embodiments, the ratchet system 770 in the slider 126 can be rotatably adjustable around the longitudinal axis 129, thereby altering the location of the ratchet system 770 relative to the ends 135, 136 of the cord 130.

Gripper System

In yet another embodiment, the slider 126 of FIG. 1 can include a cord gripper system configured to engage the ends 135, 136 of the cord 130. The gripper system may include a claw or clamping structure which clamps down on the cord 130 once installed in the slider 126. In one embodiment the gripper system may resemble the ratchet system 770 of FIG. 7, except that pawls directly engage the cord 130 rather than a toothed strip 163. The gripper system may allow the cord 130 to be pulled through the gripper system in a direction 180, generally parallel to the longitudinal axis 129 and away from the spinal vertebra 110 of FIG. 1, but not allow the cord 130 to slide in a direction 182. In another embodiment, the gripper system may clamp down on the ends 135, 136 of the cord 130 when the surgeon engages a gripping device, affixing the cord 130 to the slider 126 and not allowing motion in either direction 180, 182. The cord gripper system may be rotatably adjustable around the longitudinal axis 129, thereby altering the location of the slider 126 relative to the ends 135, 136 of the cord 130.

Decoupling the Cord from the Tensioner and the Pedicle Screw

The cord 130 can be decoupled from the tensioner 120 once a reduction procedure is complete by cutting the cord 130. For example, the cord 130 can be cut one time in the second portion 134 of the cord 130 near the first end 135. The second end 136 can be pulled in a direction 180 generally away from the pedicle screw to feed the cut end around the base of the pedicle screw and then off of the pedicle screw entirely. The second end 136 can be pulled after disconnecting the second end 136 from the tensioner 120, or it can be pulled while the second end 136 is still connected to the tensioner 120. Alternatively, the cord 130 can be cut once near the first end 135 and once near the second end 136 to disconnect the cord 130 from the tensioner 120 entirely. One of the two cut ends can then be pulled in a direction 180 generally away from the pedicle screw to feed the other cut end around the base of the pedicle screw and then off the pedicle screw. In still another aspect, the cord 130 can be removed from the tensioner by disconnecting the connectors 154, 159 from the tensioner 120. For example, the connectors 154, 159 can be pulled off of the pegs 160, 162.

The cord 130 can be temporarily affixed to the tensioner 120 before the reduction procedure. After the procedure, the cord 130 can be removed from the pedicle screw by decoupling the cord 130 from the pegs 160, 162. In another aspect, the cord 130 is permanently affixed to the tensioner 120 before the reduction procedure such that the cord 130 must be cut to remove the cord 130 from the pedicle screw and the tensioner 120 after the procedure.

Anvil

Figure 8A:
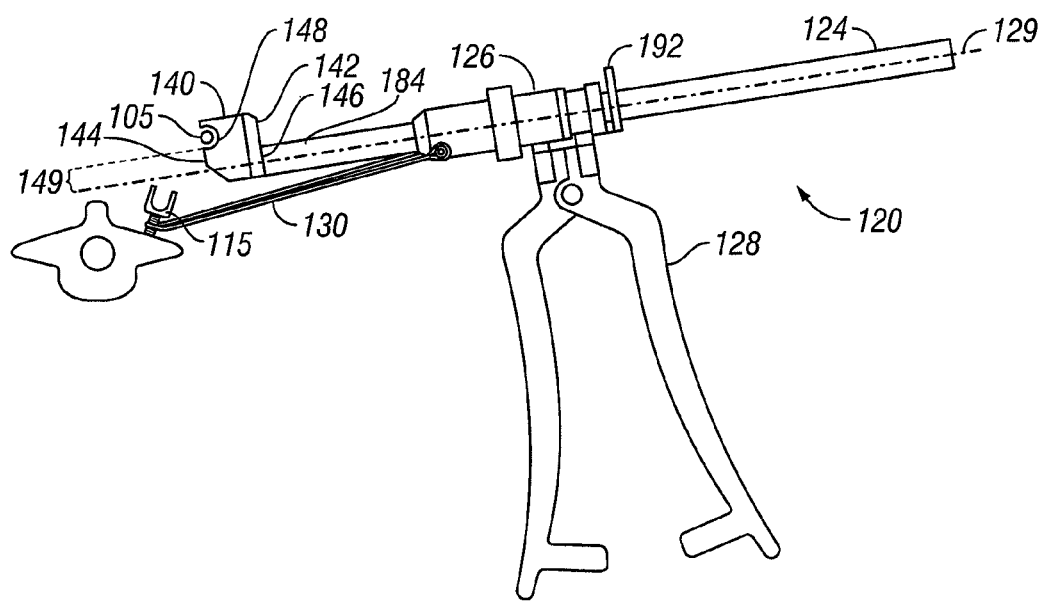
FIG. 8A is an elevational view of the spinal rod persuader system of FIG. 1 having an embodiment of an anvil.

FIG. 8A is an elevational view of an embodiment of the spinal rod persuader system 100 including an anvil 140. The first side 142 of the anvil 140 includes a tensioner engagement location 146 configured to couple to the first end 184 of the axial member 124 of the tensioner 120. The second side 144 of the anvil 140 includes a rod engagement location 148 configured to engage the spinal rod 105. The rod engagement location 148 can include a groove 148 formed in the second side 144 of the anvil 140. In some embodiments the groove 148 is offset a distance 149 from the longitudinal axis 129 of the tensioner 120.

Figure 8B:
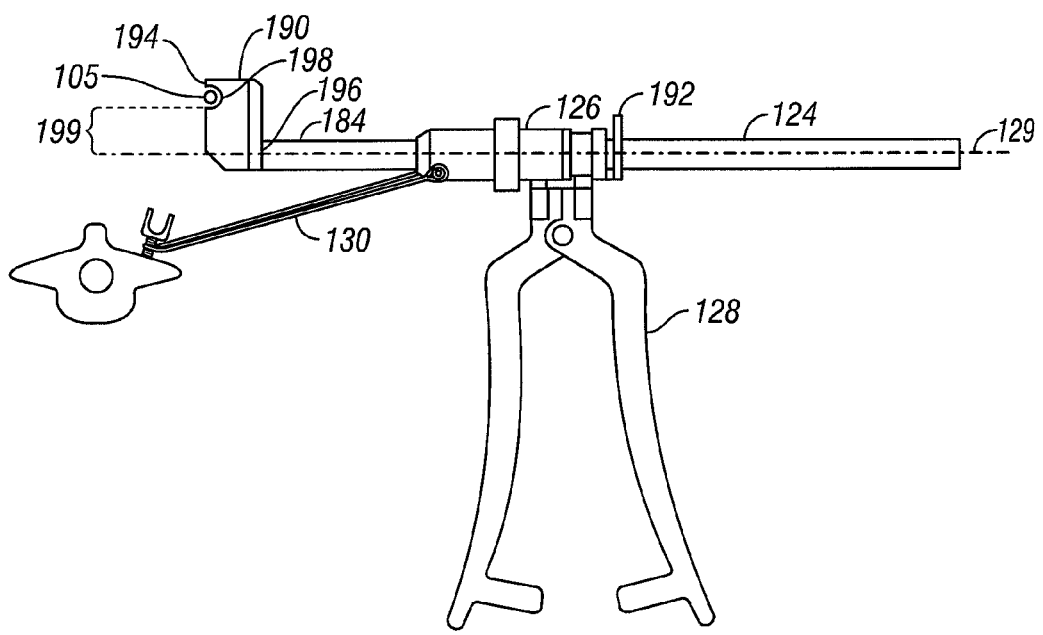
FIG. 8B is an elevational view of the spinal rod persuader system of FIG. 1 having another embodiment of an anvil.

The tensioner 120 can advantageously accept anvils of different sizes and shapes. One embodiment of the spinal road persuader system 100 provides a kit including a plurality of cords 130, a tensioner 120, and a plurality of anvils 140 of varying sizes and shapes. FIG. 8B is an elevational view of the spinal rod persuader system 100 including an anvil 190 having a different size and shape than the anvil 140 of FIG. 8A. The anvil 190 includes a rod engagement location 198 that is offset a greater distance 199 from the longitudinal axis 129 than the rod engagement location 148 of the anvil 140. Installing anvils having different offset distances 149, 199 allows the surgeon to change the angle at which the spinal rod 105 is drawn toward the pedicle screw. The kit can also include a plurality of anvils having different sized rod engagement locations 148 to engage spinal rods 105 of different diameters and configurations. Embodiments of the anvils described herein can be made of any suitable material, including but not limited to metal such as stainless steel.

Figure 9C:
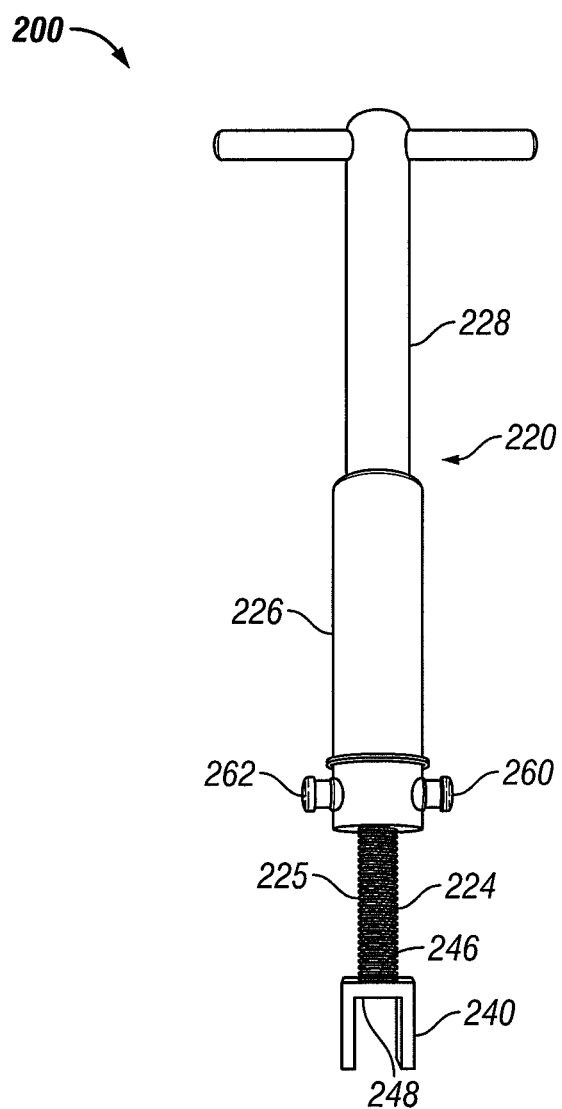
FIG. 9C is an elevational top view of the spinal rod persuader system of FIG. 9A.

FIG. 9A is a perspective view of a spinal rod persuader system 200 according to another embodiment. FIG. 9B is a perspective side view of the persuader system 200 of FIG. 9A. FIG. 9C is an elevational top view of the persuader system 200 of FIG. 9A. The persuader system 200 includes a tensioner 220, an anvil 240, and a cord 230 (not illustrated in FIGS. 9A-9C). The tensioner 220 includes a slider 226, an axial member 224, and a handle 228. When the anvil 240 is engaged with a spinal rod, rotating the handle 228 in a first direction 286 rotates the axial member 224 and linearly advances the slider 226 in the direction 280, thereby applying tension to a cord coupled to the slider 226. Rotating the handle 228 in a second direction 288 can advance the slider 226 in the direction 282. The slider 226 includes an internal thread configured to engage external threads 225 of the axial member 224, such that rotation of the axial member 224 is translated into linear motion of the slider 226 along the longitudinal axis 229 of the tensioner 220.

The tensioner can include pegs 260, 262 configured to couple the cord 230 to the tensioner 220. As described above, other configurations to couple the cord 230 to the tensioner 220 are possible. The persuader system 200 also includes an anvil 240 configured to couple to a spinal rod at a rod engagement location 248. The anvil 240 is also configured to couple to the tensioner 220 at a tensioner engagement location 246. The persuader system 200 can include anvils 240 of different sizes and shapes.

The anvil 240 can be coupled to the tensioner 220 at the tensioner engagement location 246 in a number of ways. The coupling should allow rotation of the axial member 224 while the anvil remains rotationally stationary when coupled to a spinal rod. In one alternative, the end of the axial member extends slightly through a hole in the rear of the anvil and is retained there with an e-clip or cotter pin. In another embodiment, the tensioner engagement location 246 includes a circular groove at a first end 284 of the axial member 224. The circular groove is configured to couple to a circular opening at a first side 242 of the anvil 240. The circular opening of the anvil 240 can have a larger diameter than the circular groove at the first end 284 of the axial member 224, allowing the handle 228 to spin the axial member 224 freely about the axis 229 while the anvil 240 remains coupled to a rod at the rod engagement location 248. Turning the handle 228 advances the axial member 224 in the direction 282, and advances the slider 226 in the direction 280, thereby tensioning a cord affixed to the slider 226.

In another alternative, the anvil 240 includes a U-shaped slot configured to couple to a circular groove at the first end 284 of the axial member 224. The anvil 240 and the U-shaped slot can remain stationary, affixed to the spinal rod, as the axial member 224 and the circular groove rotate about the axis 229 when the handle 228 is turned. In yet another aspect, the anvil 240 includes a ball configured to couple to a socket at the first end 284 of the axial member 224. Alternatively, the anvil 240 includes a socket configured to couple to a ball at the first end 284 of the axial member 224. The ball-and-socket couplers allow the anvil 240 to remain stationary, affixed to the spinal rod, as the axial member 224 spins about the axis 229.

In still another alternative, the first end 284 of the axial member 224 includes a receiver configured to accept a dowel of the anvil 240. Alternatively, the axial member 224 includes a dowel configured to mate with a receiver of the anvil 240. The dowel-and-receiver couplers allow the axial member 224 to spin freely about the substantially stationary anvil 240 when the handle 228 is turned. The dowel-and-receiver couplers can advantageously allow a first anvil 240 to be easily replaced with a second anvil 240 of a different size and/or shape before or during a reduction procedure. Other configurations that allow a rotationally-free coupling between the axial member 224 and the anvil 240 are possible.

Method of Spinal Rod Persuasion

A spinal rod 105 may be pulled towards a spinal vertebra 110 during spinal surgery using embodiments of the spinal rod persuader system 100 described herein. If, for example, a spinal curvature is being corrected by fixing the spine to a rigid spinal rod, two pedicle screws of a pedicle screw system may be installed at separated positions (e.g. near the top, and near the bottom) of the spine. Two ends of the spinal rod 105 are fixed to the two pedicle screws. The spinal rod 105 may be installed in the cups 115 of the two pedicle screws, for example. A surgeon affixes a cord 130 to another pedicle screw installed in a spinal vertebra 110 of the spine at an intermediate location. In one aspect, the surgeon loops the cord 130 around a base of the pedicle screw at least once and pulls the ends 135, 136 of the cord 130 so that the loop 138 wraps tightly around the base of the pedicle screw, thereby affixing the cord 130 to the pedicle screw. The surgeon may use a mark 139 at the midpoint of the cord 130 to ensure that the loop 138 is centered on the pedicle screw. In another aspect, the surgeon affixes a cord 330 having a pre-formed lasso 338 to the pedicle screw. The surgeon can place the lasso 338 over the pedicle screw and rest the lasso 338 adjacent to the base of the pedicle screw. The surgeon can then pull on the ends 335, 336 of the cord 330, cinching the lasso 338 tight around the base of the pedicle screw. Based on the needs of the patient during a particular reduction procedure, the surgeon can install the cord 130, the cord 330, or a different cord from a kit including different cords.

Next, the surgeon couples the ends 135, 136 of the cord 130 to the tensioner 120 by affixing the ends 135, 136 to the slider 126. In one embodiment, the surgeon places a first eye splice 154 on the first end 135 of the cord 130 over a first peg 160 located on the slider 126, and places a second eye splice 159 on the second end 136 of the cord 130 over a second peg 162 on the slider 126.

Next, the surgeon couples the anvil 140 to the tensioner 120 and couples the spinal rod 105 to the anvil 140. The anvil 140 is coupled to the spinal rod 105 by maneuvering the rod engagement location 148 in a position to engage the spinal rod 105. The surgeon then moves the slider 126 along the axial member 124 towards the second end 185 of the axial member 124 by repeatedly activating the handle 128 of the tensioner 120. The surgeon can activate the handle 128 by squeezing the handle 128, for example. Activating the handle 128 can create tension in the cord 130 and pull the spinal vertebra 110 toward the spinal rod 105. In another embodiment described with reference to FIGS. 9A-9C, the handle is activated by rotating the handle, causing the slider to move away from the vertebra and tensioning the cord coupled to the slider. In some aspects, the surgeon advances the slider 126 along the axial member 124 until the anvil 140 touches or nearly touches the spinal rod 105, then pushes the rod into a receiver or cup of the pedicle screw by hand. In embodiments including a kit having various anvils 140, the surgeon can install any size anvil 140 before or during a reduction procedure to facilitate the optimal angle at which the pedicle screw is drawn toward the spinal rod 105.

Advantages

The spinal rod persuader systems described herein can manipulate the spinal vertebra 110 in more than one plane during a reduction procedure. Embodiments of the spinal rod persuader systems can also reduce the risk of pulling the pedicle screw out of the spinal vertebra 110 during a reduction procedure due to the oblique angle at which the cord 130 pulls the pedicle screw.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments.

What is claimed is:

1. A system for moving a pedicle screw installed in a spinal vertebra toward a spinal rod, the system comprising:
    a pedicle screw;
    a cord comprising a first portion and a second portion, the first portion configured to wrap around a base of the pedicle screw;
    a spinal rod;
    a tensioner configured to engage the spinal rod, the second portion of the cord comprising one or more loop connectors directly coupled to pegs on the tensioner such that the cord can be oriented at various angles relative to the spinal rod, the tensioner configured to pull the second portion of the cord, thereby moving the pedicle screw toward the spinal rod; and
    a plurality of anvils, each anvil comprising a tensioner engagement location on a first side the tensioner engagement location configured to couple to a first longitudinal end of the tensioner, each anvil further comprising a rod engagement location on a second side, the rod engagement location configured to engage the spinal rod.

2. The system of claim 1, wherein the one or more loop connectors comprise eye splices.

3. The system of claim 1, wherein the first portion of the cord comprises a lasso at a midpoint of the cord.

4. The system of claim 3, wherein the lasso is formed by inserting a first end of the cord into the first portion of the cord.

5. The system of claim 1, wherein the tensioner comprises a slider configured to move along a longitudinal axis of the tensioner.

6. The system of claim 5, wherein the tensioner comprises a handle configured to move the slider along the longitudinal axis of the tensioner.

7. The system of claim 1, wherein a distance between the rod engagement location of a first anvil and a longitudinal axis of the tensioner is greater than the distance between the rod engagement distance of a second anvil and the longitudinal axis of the tensioner.

8. The system of claim 1, wherein an offset between the longitudinal axis of the tensioner and the rod engagement location of a first anvil is less than an offset between the longitudinal axis and the rod engagement location of a second anvil.

9. The system of claim 1, wherein the cord is configured to pass over a top side of an anvil coupled to a first longitudinal end of the tensioner.

10. The system of claim 1, wherein the tensioner comprises an anvil having a groove sized to engage the spinal rod.

11. A system for moving a pedicle screw installed in a spinal vertebra toward a spinal road, the system comprising a cord comprising a first portion configured to wrap around a base of the pedicle screw and a tensioner configured to engage the spinal rod, the cord comprising a second portion configured to couple to the tensioner, the second portion of the cord comprising one or more toothed strips, the tensioner configured to pull the second portion of the cord, thereby moving the pedicle screw toward the spinal rod.

12. The system of claim 11, wherein the tensioner comprises a slider configured to move along a longitudinal axis of the tensioner, the toothed strips configured to couple to the slider.

13. The system of claim 11, further comprising a plurality of anvils, each anvil comprising a tensioner engagement location on a first side, the tensioner engagement location configured to couple to a first longitudinal end of the tensioner, each anvil further comprising a rod engagement location on a second side, the rod engagement location configured to engage the spinal rod.

14. The system of claim 11, wherein pulling the second portion of the cord pulls the pedicle screw at an oblique angle.

15. A system for pulling a pedicle screw installed in a spinal vertebra toward a spinal rod, the system comprising:
   a pedicle screw configured for installation in a spinal vertebra;
   a spinal rod;
   a tensioner having a first longitudinal end and a second longitudinal end disposed along a longitudinal axis of the tensioner;
   a slider mounted to the tensioner and configured to move along the longitudinal axis of the tensioner toward the second longitudinal end;
   an anvil comprising a groove engaged with the spinal rod, the anvil coupled to a first part of the tensioner proximate the first longitudinal end;
   a cord having a first portion connected to the pedicle screw configured for installation in the spinal vertebra, a second portion of the cord comprising one or more loop connectors directly coupled to pegs on the slider at a second, different part of the tensioner such that the cord can be oriented at various angles relative to the spinal rod; and
   a plurality of anvils interchangeably connectable to the first longitudinal end of the tensioner,
   wherein the tensioner is configured to pull the second portion of the cord by moving the slider along the longitudinal axis toward the second longitudinal end, and wherein pulling the second portion of the cord pulls the pedicle screw at an oblique angle.

16. The system of claim 15, wherein the first portion of the cord comprises a lasso wrapped around a base of the pedicle screw.

17. The system of claim 15, wherein each anvil comprises a different sized groove to engage spinal rods of different diameters.

18. The system of claim 15, wherein each anvil comprise a groove configured to engage a spinal rod, and wherein an offset between the longitudinal axis of the tensioner and the groove of a first anvil is less than an offset between the longitudinal axis and the groove of a second anvil.

* * * * *

UNITED STATES PATENT AND TRADEMARK OFFICE
CERTIFICATE OF CORRECTION

| | | |
|---|---|---|
| PATENT NO. | : 8,932,296 B2 | Page 1 of 1 |
| APPLICATION NO. | : 13/246631 | |
| DATED | : January 13, 2015 | |
| INVENTOR(S) | : Neary et al. | |

It is certified that error appears in the above-identified patent and that said Letters Patent is hereby corrected as shown below:

On the title page, item (75) in the listing of inventors, please add Jeffrey Eugene Deckey as an inventor, thus providing a list of inventors as follows:

Douglas Wayne Neary

James Monroe Davenport

Jeffrey Eugene Deckey

Signed and Sealed this
Eighth Day of March, 2016

Michelle K. Lee
*Director of the United States Patent and Trademark Office*